United States Patent [19]

Tilly et al.

[11] 4,062,934
[45] Dec. 13, 1977

[54] X-RAY CONTRAST MEDIA

[75] Inventors: Guy Tilly; Michel Jean-Charles Hardouin; Jean Lautrou, all of Aulnay-Sous-Bois, France

[73] Assignee: Laboratoires Andre Guerbet, Aulnay-Sous-Bois, France

[21] Appl. No.: 689,929

[22] Filed: May 25, 1976

[30] Foreign Application Priority Data

June 4, 1975 United Kingdom ............. 24118/75

[51] Int. Cl.² .................... A61K 29/02; C07C 103/82
[52] U.S. Cl. .................................. 424/5; 260/559 A
[58] Field of Search ....................... 424/5; 260/559 A

[56] References Cited

U.S. PATENT DOCUMENTS

| | | | |
|---|---|---|---|
| 3,178,473 | 4/1965 | Holtermann et al. | 424/5 X |
| 3,290,366 | 12/1966 | Hoey | 424/5 X |
| 3,306,927 | 2/1967 | Larsen | 424/5 X |
| 3,541,141 | 11/1970 | Bernstein et al. | 424/5 X |
| 3,557,197 | 1/1971 | Felder et al. | 424/5 X |
| 3,660,469 | 5/1972 | Bernstein et al. | 424/5 X |
| 3,701,771 | 10/1972 | Almen et al. | 424/5 X |
| 3,732,293 | 5/1973 | Ackerman | 424/5 X |
| 3,939,204 | 2/1976 | Buttermann | 424/5 X |
| 4,005,188 | 1/1977 | Tilly et al. | 424/5 |
| 4,014,986 | 3/1977 | Tilly et al. | 424/5 |

Primary Examiner—Daniel E. Wyman
Assistant Examiner—Thomas A. Waltz
Attorney, Agent, or Firm—Young & Thompson

[57] ABSTRACT

This invention relates to compounds having the following general formula:

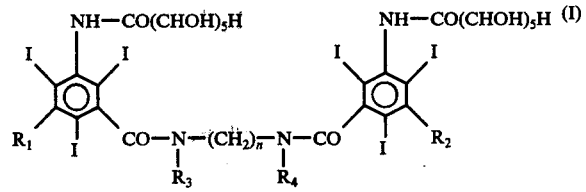

in which $n$ is an integer from 0 to 4; $R_1$ and $R_2$ represent independently from each other a radical of the formula —$CONHR_5$ in which $R_5$ is an alkyl radical having 1–4 carbon atoms or a hydroxyalkyl radical having 1–4 carbon atoms or a radical of the formula

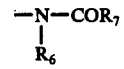

in which $R_6$ and $R_7$ are alkyl radicals having 1–4 carbon atoms; and $R_3$ and $R_4$, independently from each other, represent a hydrogen atom or an alkyl radical having 1–4 carbon atoms.

Said compounds are useful as X-ray contrast media, particularly for myelography.

3 Claims, No Drawings

X-RAY CONTRAST MEDIA

This invention relates to new water-soluble non-ionic tri-iodo benzene derivatives useful as X-ray contrast media, particularly for myelography.

U.S. Pat. No. 3,701,771 discloses non-ionic compounds useful as X-ray contrast media, particularly tri-iodo benzamide derivatives.

This invention relates to new non-ionic compounds having good solubilities and which are markedly better tolerated than the known materials.

Such compounds have the general formula:

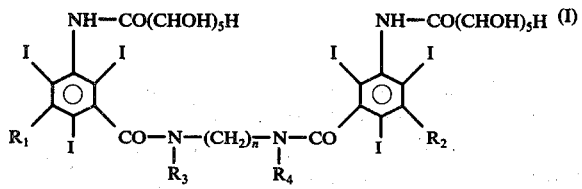

in which:

$n$ is an integer from 0 to 4, $R_1$ and $R_2$, independently from each other, represent a radical of the formula $-CONHR_5$ in which $R_5$ is an alkyl radical having 1-4 carbon atoms or a hydroxyalkyl radical having 1-4 carbon atoms or a radical of the formula

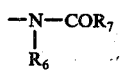

in which $R_6$ and $R_7$ are alkyl radicals having 1-4 carbon atoms, and $R_3$ and $R_4$, independently from each other, represent a hydrogen atom or an alkyl radical having 1-4 carbon atoms.

The compounds of the formula (I) may be prepared by reaction of an acid halide of the formula HalCO(CHOH)$_5$H, in which the hydroxy groups are protected, with a diamine of the formula:

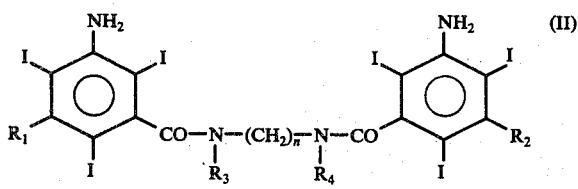

in which $n$, $R_1$, $R_2$, $R_3$ and $R_4$ have the meanings given for formula (I), followed by saponification of the condensation product.

The condensation reaction of the acid chloride with diamine (II) is advantgeously effected within a polar solvent such as dimethylacetamide or dimethylsulfoxide, at a temperature of about 15° C to about 35° C. A substantially complete reaction is generally obtained after stirring during 1-4 days.

The amines of the formula (II) may be prepared by condensation of an amine of the formula:

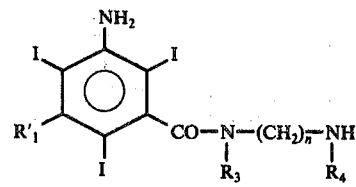

in which $R'_1$ has the meaning given for $R_1$ or represents a group $-COOH$, and $n$, $R_3$ and $R_4$ have the meanings given for the formula (I), with an acid chloride having the formula:

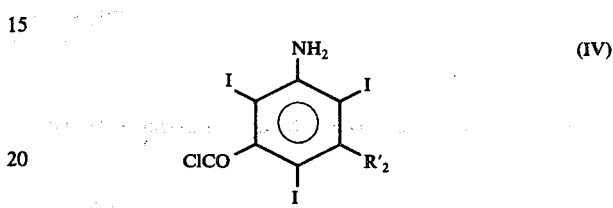

in which $R'_2$ is a radical identical with $R_2$ but in which any hydroxy groups are protected, followed, in the case where $R'_1$ is a group $-COOH$, by amidification to a group $-CONHR_5$ (in conventional manner, via the acid chloride and action of an amine $NH_2R_5$).

The condensation reaction of amine (III) with the acid chloride is advantageously effected within a polar solvent such as dimethylacetamide, dimethylformamide or dimethylsulfoxide at a temperature of 20-60° C, in the presence of excess acid binding agent such as triethylamine or sodium carbonate. The reaction time may vary from 2 hours to about 4 days.

The amines of the formula (II) in which $R_1$ and $R_2$ are the same may also be prepared by condensing a diamine of the formula:

in which $n$, $R_3$ and $R_4$ have the meanings given for the formula (I), with an acid chloride of the formula (IV). The reaction conditions are the same as in the case of condensation with an amine of the formula (III).

The amines of the formula (II), in which $R_1$ and $R_2$ are the same and represent a radical $-CONHR_5$, may also be prepared according to a modification essentially comprising effecting the condensation with non-iodo compounds and effecting the iodination at the final stage.

This modification comprises:

a. condensing a diamine of the formula (V) with an acid chloride of the formula:

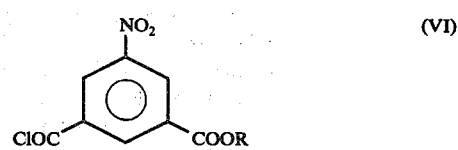

in which R is an alkyl radical having 1-4 carbon atoms, particularly methyl, to give a diester of the formula:

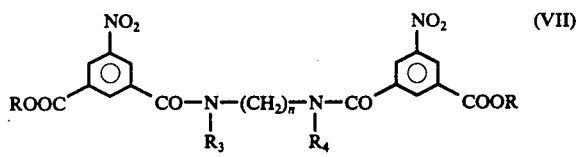

b. reacting the diester of the formula (VII) with an amine of the formula NH$_2$R$_5$, to give a diamide of the formula:

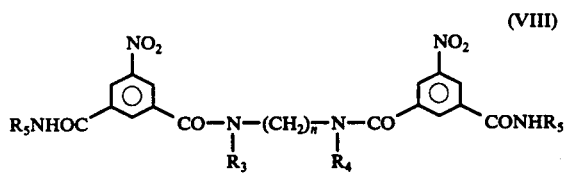

c. reducing the nitro groups of the diamide of the formula (VIII), to give a diamine having the formula:

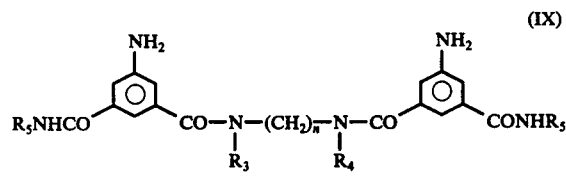

d. iodinating the compound of the formula (IX), to give a diamine having the formula:

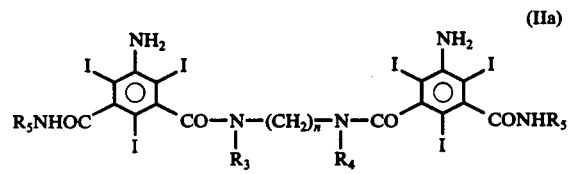

The condensation of a diamine of the formula (V) with an acid chloride of the formula (VI) may be effected in an alkaline medium or in dioxan (under the usual temperature conditions for the type of condensation, e.g., between room temperature and 50° C). The reaction of a diester of the formula (VII) with an amine of the formula NH$_2$R$_5$ may be effected in solution in the amine to which water or an alcohol may be added, under the usual temperature conditions. The reduction of the nitro groups of the diamide (VIII) may be effected catalytically (for example in the presence of Raney nickel or palladium).

The iodination of the compounds of the formula IX may be effected according to the usual methods for the halogenation of benzene nuclei, typically by action of iodine chloride in acidic medium.

It is also possible to alkylate a diamine of the formula (II) in which R$_3$ and/or R$_4$ are hydrogen atoms, to give a diamine in which R$_3$ and R$_4$ are alkyl radicals. For this purpose, the usual alkylating methods may be used, for example using a suitable alkyl iodide or alkyl sulfate.

The following non-limiting Examples illustrate the preparation of compounds of the formula (I).

EXAMPLE I Preparation of
1,2-N,N'-bis(2,4,6-triiodo-3-N-methyl-N acetylamino-5-N-gluconylamino -benzoyl)-diamino-ethane

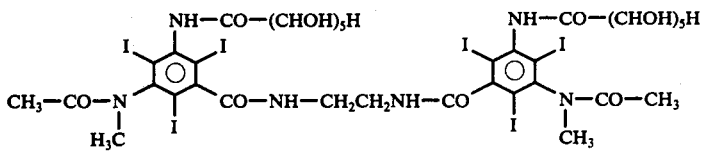

(a) Preparation of
1,2-N,N'-bis(2,4,6-triiodo-3-N-methyl-N-acetylamino-5-amino-benzoyl)diamino-ethane To a solution of 2,4,6-triiodo-3-N-methylacetamido-5-amino-benzoic acid chloride (280 g; 0.465 mole)(prepared according to the teachings of British Patent 1,321,592) in dimethylacetamide (500 ml) and triethylamine (130 ml; 0.93 mole) is added ethylene diamine (18.7 ml; 0.29 mole) with stirring, without exceeding a temperature of 25° C. After stirring overnight at room temperature, the material is analyzed chromatographically to ascertain there is no starting acid chloride left. The reaction liquor is poured over ice-water (3 liters) with stirring. The resulting precipitate is suction filtered, washed with water and dried in an oven at 70° C, to give 186 g of fairly coloured material which is purified by dissolution in dimethylacetamide (300 ml) and fractional precipitation by addition of water. A very light beige product (132 g) is obtained after washing with water, suction filtering and drying. Purity of the product is controlled by:
Thin-layer chromatography, Silicagel plate, eluent: benzene/methylethylketone/formic acid (60:25:20).
Starting acid chloride: Rf = 0.80
Condensation product: Rf = 0.45
Iodine titration = 98%.

(b) Preparation of
1,2-N,N'-bis(2,4,6-triiodo-3-N-methyl-N-acetylamino-5-N-gluconylamino-benzoyl)-diamino-ethane To a solution of 1,2-N,N'-bis(2,4,6-triiodo-3-N-methyl-N-acetylamino-5-amino-benzoyl)diamino-ethane (121 g; 0.101 mole) in dimethylacetamide (200 ml) is added, portionwise, penta-acetyl gluconic acid chloride (172 g; 0.404 mole [prepared according to C. E. Braun and C. D. Cook, Organic Syntheses, Vol. 41, pp. 79–82]. After stirring during 4 days at 20°-25° C, the reaction liquor is poured over ice-water (1 liter), with vigorous stirring. The crystalline material is suction filtered, washed with ice-water, suction filtered and the wet material is added to water (100 ml) and ammonia (200 ml) to saponify the ester functions.

After stirring during 16 hours at 20°-25° C, the water and excess ammonia are evaporated in vacuo, to give a thick oil (210 g) which is dissolved in water (300 ml).

The aqueous solution is extracted twice, with 200 g and 100 g of phenol. The organic phase is washed with 4 × 60 ml water, diethyl ether (1 liter) is added; the resulting material is extracted with 4 × 100 ml water; the aqueous phase is washed with 3 × 150 ml diethyl ether. The resulting material is evaporated in vacuo, to give 135 g of half-gummy - half-crystalline material.

The purity of the crude product is controlled by:
Thin-layer chromatography, Silicagel plate, eluent: butanol/acetic acid/water (50:11:25).
  Starting amine Rf = 0.60 - 0.65 (2 isomers)
  Condensation product prior to saponification: Rf between 0.52 and 0.57
  Condensation product after saponification: Rf = 0.12 - 0.18 - 0.23 (3 isomers)
Iodine titration = 87% purity.

The crude material is dissolved in water (50 ml) and ethyl alcohol (500 ml) is added thereto, with stirring. The resulting precipitate is suction filtered, washed with ethyl alcohol and dried at 60° C, to give 64.5 g of product which is crystallized twice from ethyl alcohol (an insoluble material is removed in the hot).

The resulting material is charcoaled during 16 hours at 60° C, in 50% aqueous solution; the charcoal is filtered off and the water is evaporated off in vacuo. The resulting powder is dried in an oven at 80° C, to give 9 g of product.

Purity of this product is controlled by:
Thin-layer chromatography over Silicagel plate; eluent: butanol/acetic acid/water (50:11:25).
  There are 3 isomers: Rf = 0.12 - 0.18 - 0.23.
Iodine titration = 99% purity.
Titration with sodium methoxide: 103% purity.

c. Dissolution

The product is dissolved in water at a concentration of 25 g iodine per 100 ml. The solution has a viscosity of 7.4 centipoises at 37° C.

EXAMPLE II

Preparation of N,N'-bis(2,4,6-triiodo-3-N-methyl-N-acetylamino-5-N-gluconylamino-benzoyl)hydrazide

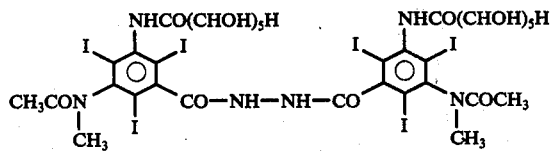

(a) Preparation of 2,4,6-triiodo-3-N-methyl-N-acetylamino-5-amino-benzohydrazide

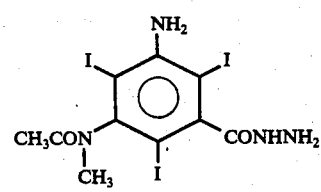

To a solution of hydrazine hydrate (98%; 372 ml; 7.45 moles) and water (500 ml) is added 2,4,6-triiodo-3-N-methyl-N-acetylamino-5-amino-benzoic acid chloride (1500 g; 2.38 moles) dissolved in dioxan (3 liters), while cooling and with vigorous stirring.

After 5 hours reaction at 20° C, the precipitate is suction filtered and washed with water, after which it is dried in an oven at 100° C, to give 755 g of white material (Yield: 50%)

Purity of the product is controlled by:
Iodine titration = 100%
Titration with perchloric acid: 98.5%.
Thin-layer chromatography over silicagel plate; eluent: benzene/methylethylketone/formic acid (60:25:20).
  Starting acid chloride: Rf = 0.80
  Condensation product: Rf = 0.70.

(b) Preparation of N,N'-bis(2,4,6-triiodo-3-N-methyl-N-acetylamino-5-amino-benzoyl)hydrazide

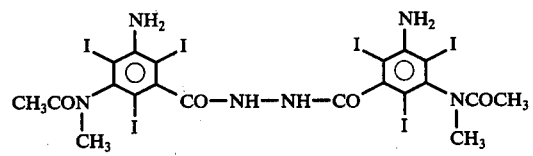

The product obtained in step (a) (750 g; 1.25 mole) is dissolved in dimethylacetamide (1.250 liter) plus potassium carbonate (345 g; 2.5 moles) and 2,4,6-triiodo-3-N-methyl-N-acetylamino-5-amino-benzoic acid chloride (755 g; 1.25 mole) is added thereto, with stirring. After heating at 50° C during 2 days, with stirring, the reaction liquor is poured over water (7.5 liters), and then neutralized to pH 7 with hydrochloric acid; the resulting precipitate is suction filtered and washed with water. The wet material is purified by heating at 70° C, during 4 hours, in methanol (4 liters). It is then suction filtered and dried, to give 869 g of product (Yield: 60%). Purity of the product is controlled by:
Iodine titration: 97%
Thin-layer chromatography over silicagel plate; eluent: benzene/methylethylketone/formic acid (60:25:5).
  Starting acid chloride: Rf = 0.70
  Starting amino compound: Rf = 0.60
  Condensation product: 2 isomers: Rf = 0.30–0.22.

(c) Preparation of N,N'-bis(2,4,6-triiodo-3-N-methyl-N-acetylamino-5-N-gluconylamino-benzoyl)hydrazide To N,N'-bis(2,4,6-triiodo-3-N-methyl-N-acetylamino-5-amino-benzoyl)hydrazide (400 g; 0.342 mole) dissolved in dimethylacetamide (700 ml) is added pentaacetylated gluconic acid chloride (725 g; 1.71 mole).

After stirring during 48 hours at room temperature, the reaction liquor is poured over water (5 liters). The resulting precipitate is washed twice with hot water and is then suction filtered. The ester functions are saponified by adding the wet material to sodium hydroxide pellets (192 g) dissolved in water (2 liters). The resulting mixture is stirred during 4 hours at room temperature and is then made acidic to pH 2–3 with acetic acid. The aqueous solution is extracted with phenol (600 g and 400 g); the organic phase is washed with 4 × 500 ml water, diluted with diethyl ether (3 liters), extracted with 2 × 500 ml water, and washed with 4 × 400 ml diethyl ether. After charcoaling, the aqueous solution is evaporated in vacuo, to give 378 g amorphous material (Yield: 72%). The purity of the crude product is controlled by:
Iodine titration: 95%
Thin-layer chromatography over silicagel plate; eluent: butanol/acetic acid/water (50:11:25)
  Starting amine: Rf = 0.75 - 0.80 (2 isomers)
  Condensed product prior to saponification: Rf = 0.68 - 0.72

Condensed product after saponification: Rf = 0.18 - 0.22 - 0.12 (3 isomers).

The crude material (130 g) is dissolved in water (100 ml) and slowly added to ethanol (600 ml), with stirring. The crystalline material is suction filtered and washed with ethanol, to give 83 g dry product which is dissolved in water (70 ml). The aqueous solution is added to ethanol (400 ml), with stirring. The resulting material is suction filtered and washed with ethanol, after which it is dried, to give 37 g of almost white product (Yield: 28%. The purity of the purified product is controlled by:

Thin-layer chromatography over silicagel plate; eluent: butanol/acetic acid/water (50:11:25)
  Presence of 2 or 3 isomers, according to the drying of the plate: Rf = 0.12, 0.18, 0.22.
Iodine titration: 98%
Titration with sodium methoxide: 99.5%.

EXAMPLE III

Preparation of N,N'-bis(2,4,6-triiodo-3-N-methyl-N-acetylamino-5-N-gluconylamino-benzoyl)dimethyl hydrazide

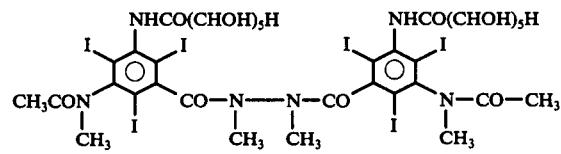

(a) Preparation of N,N'-bis(2,4,6-triiodo-3-N-methyl-N-acetylamino-5-amino-benzoyl)dimethyl hydrazide

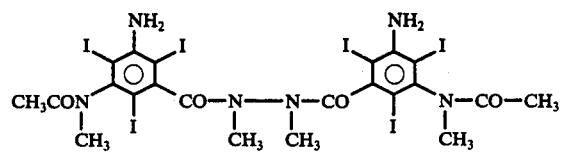

N,N'-bis(2,4,6-triiodo-3-N-methyl-N-acetylamino-5-amino-benzoyl)hydrazide (117 g; 0.1 mole) is stirred with 2N sodium hydroxide (200 ml) and acetone (150 ml), after which dimethyl sulfate (38 ml; 0.4 mole) is added thereto, with vigorous stirring. After 24 hours, the precipitate is suction filtered and washed 3 times with warm water, to give 110 g dry material (Yield: 91%). This is then washed during 24 hours in refluxing methanol (250 ml), to give 97 g dry product. The purity of the product is controlled by:

Thin-layer chromatography over silicagel plate; eluent: benzene/methylethylketone/formic acid (60:25:5)
  Unmethylated product: Rf = 0.22 - 0.30 (2 isomers)
  Methylated product: Rf = 0.45 - 0.50.

(b) Preparation of N,N'-bis(2,4,6-triiodo-3-N-methyl-N-acetylamino-5-gluconylamino-benzoyl)dimethyl hydrazide To a solution of the above product (95 g; 0.08 mole) in dimethylacetamide (160 ml) is added pentaacetylated gluconic acid chloride (170 g; 0.40 mole). After stirring during 48 hours at 20° C, the reaction liquor is poured over water (1.6 liter), washed twice with water and suction filtered. The ester functions are saponified by adding the wet material to water (200 ml) plus 10N sodium hydroxide (128 ml). After stirring during 4 hours at 20° C, the mixture is neutralized to pH 5-6 with hydrochloric acid, and a slight precipitate is suction filtered. The product is extracted with phenol, according to the previously described procedure, to give 83 g of product, after evaporation to dryness:

Iodine titration: 95%
Thin-layer chromatography over silicagel plate; eluent: butanol/acetic acid/water (50:11:25). Rf = 0.15–0.20–0.25 (3 isomers).

The product is purified by treating twice with water-ethanol, to give 15 g of product.

EXAMPLE IV

Preparation of N,N'-bis(2,4,6-triiodo-3-N-hydroxyethyl-carbamyl-5-gluconylamino-benzoyl)hydrazide

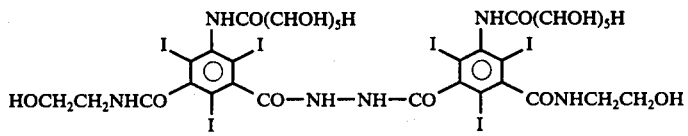

(a) Preparation of N,N'-bis(3-methoxycarbonyl-5-nitro-benzoyl)hydrazide

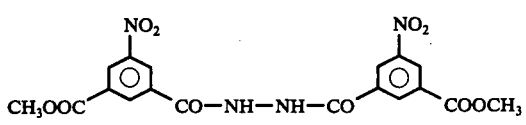

To a suspension of 3-methoxycarbonyl-5-nitro-benzoic acid chloride (1000 g; 4.1 moles) in water (4 liters) is added hydrazine hydrate (105 ml) and sodium hydroxide (102 g) in water (400 ml). After 1 hour, sodium hydroxide (100 g) in water (400 ml) is added. The resulting mixture is stirred during 25 hours, after which it is made acidic, and the resulting material is filtered off and washed with water, to give 900 g dry product (Yield: 98%).

Thin-layer chromatography over silicagel plate; eluent: benzene/methylethylketone/formic acid (60:25:20):
  Starting material: RF = 0.90
  Condensed product: Rf = 0.80.

(b) Preparation of
N,N'-bis(3-N-hydroxyethylcarbamyl-5-nitro-benzoyl)-hydrazide

N,N'-bis(3-methoxycarbonyl-5-nitro-benzoyl)hydrazide (575 g; 1.29 mole) is added to ethanolamine (1.5 liter) and methanol (1 liter). After stirring during 20 hours, the reaction mixture is diluted with water (1 liter) and poured over water (10 liters) and hydrochloric acid (2 liters). The resulting material is suction filtered, and then dried in an oven, to give 694 g of product which is purified by washing in refluxing ethanol. It is then dried, to give 538 g of product (Yield: 83%).
Thin-layer chromatography over silicagel plate; eluent: butanol/acetic acid/water (50:11:25),
Diester product: RF = 0.90
Amidified product: Rf = 0.08.

(c) Preparation of
N,N'-bis(3-N-hydroxyethyl-carbamyl-5-aminobenzoyl)hydrazide

The nitro derivative obtained in step (b) (326 g/ 0.65 mole) is added to hydrazine hydrate (365 ml), water (3.5 liters) and Raney nickel. After stirring during 20 hours, the reaction mixture is acidified to pH 3, filtered and precipitated by addition of 10N sodium hydroxide to pH 5–6. The resulting material is filtered off, washed with water, to give 300 g of dry material the purity of which is controlled by:
Thin-layer chromatography over silicagel plate; eluent: butanol/acetic acid/water (40:11:25),
Nitro product: Rf = 0.05
Reduced product: Rf = 0.45.

(d) Preparation of
N,N'-bis(2,4,6-triiodo-3-N-hydroxyethyl-carbamyl-5-amino-benzoyl)hydrazide

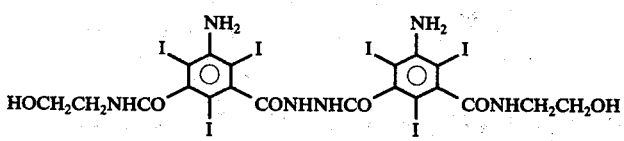

To a solution of N,N'-bis(3-N-hydroxyethyl-carbamyl-5-amino-benzoyl)hydrazide product (300 g; 0.67 mole) in water (4.1 liters) and hydrochloric acid (170 ml), is added a solution of iodine chloride (250 ml) in potassium chloride (375 g) dissolved in water (1.6 liter). After stirring overnight at 60° C, the material is treated with bisulfite, suction filtered and washed with water, to give 570 g crude product. The product is purified by dissolution in 0.2N sodium hydroxide (1100 ml) and salting out with 17N sodium hydroxide. The crystalline material is dissolved in water, after which it is made acidic with hydrochloric acid and washed with water, to give 150 g dry product, the purity of which is controlled by:
Thin-layer chromatography over silicagel plate; eluent: benzene/methylethylketone/formic acid (60:25:20):
Rf of the starting material: 0.15
Rf of the iodo product: 0.25
Iodine titration: 97% purity.

(e) Preparation of
N,N'-bis(2,4,6-triiodo-3-N-hydroxyethyl-carbamyl-5-gluconylamino-benzoyl)hydrazide

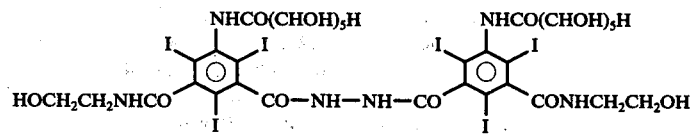

To a solution of N,N'-bis(2,4,6-triiodo-3-N-hydroxyethyl-carbamyl-5-amino-benzoyl)hydrazide (60 g; 0.05 mole) in dimethylacetamide (200 ml) is added pentaacetylated gluconic acid chloride (210 g; 0.5 mole). The reaction mixture is stirred during 24 hours at 20°–25° C and is then poured over water (1 liter), suction filtered and washed with water. The ester functions are saponified by treating the wet material with 2N sodium hydroxide (1.2 liter) during 2 hours. The solution is then acidified to pH 6 with hydrochloric acid and treated three times with 3 SA carbon black. The solution is extracted with phenol, according to the previously described procedure. It is then evaporated to dryness, to give 58 g crude product.
Thin-layer chromatography over silicagel plate; eluent: butanol/acetic acid/water (50:11:25),
Amino product: Rf = 0.70
Gluconic ester product: Rf = 0.75
Saponified product: Rf = 0.15.

The crude product is purified by fractional crystallization from water-ethanol, to give 14 g of purified product the purity of which is controlled by:
Iodine titration: 97% purity Thin-layer chromatography over silicagel plate; eluent: butanol/acetic acid/water (50:11:25): Rf = 0.15.

EXAMPLE V

Preparation of 1,2-N,N'-bis(2,4,6-triiodo-3-N-hydroxyethylcarbamyl-5-N-gluconylamino-benzoyl)diamino-ethane (a) 2,4,6-Triiodo-3-N-acetoxyethylcarbamyl-5-amino-benzoic acid

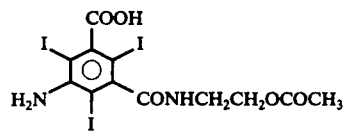

2,4,6-Triiodo-3-N-hydroxyethylcarbamyl-5-amino-benzoic acid (133 g; 0.22 mole) is dissolved in pyridine (500 ml). Acetic acid (13.8 ml; 0.23 mole) and N,N'-dicyclohexylcarbodiimide (50 g; 0.243 mole) are added thereto and the resulting material is stirred during 16 hours at room temperature. The precipitate is suction filtered and acetic acid (6.9 ml; 0.115 mole) and N,N'-dicyclohexylcarbodiimide (25 g; 0.12 mole) are added to the filtrate. After stirring 24 hours at room temperature, the precipitate is suction filtered, the filtrate is evaporated to dryness, the concentrate is taken up into water (500 ml), stirred 24 hours at room temperature, after which the precipitate is suction filtered, washed with water and dried, to give 103 g (Yield = 73%) of 2,4,6-triiodo-3-N-acetoxyethylcarbamyl-5-amino-benzoic acid. The purity of the product is controlled by:
1/ Thin-layer chromatography over Silicagel plate in eluent: benzene/methylethylketone/formic acid (60:25:20):
Rf: starting material = 0.55
Rf: acetyl compound = 0.65
2/ Titration with tetrabutyl hydroxy ammonium 0.1N = 94%
Iodine titration = 94%

(b) 2,4,6-Triiodo-3-N-acetoxyethylcarbamyl-5-amino-benzoic acid chloride

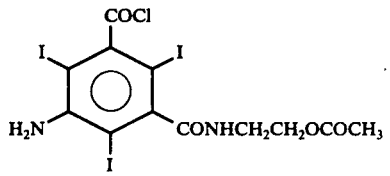

2,4,6-Triiodo-3-N-acetoxyethylcarbamyl-5-amino-benzoic acid (103 g; 0.160 mole) is dissolved in thionyl chloride (250 ml). The solution is heated 2 hours at 60° C, after which it is evaporated to dryness, the concentrate is taken up into benzene (200 ml) and then evaporated to dryness, to give 106 g (Yield: 100%) acid chloride which is used without further purification. Purity of the material is controlled by thin-layer chromatography over Silicagel plate in eluent: benzene/methylethylketone/formic acid (60:25:20).
Rf: starting acid = 0.65
Rf: acid chloride = 0.9
Rf: after condensation with ethanolamine = 0.35
Rf: after condensation with ethanolamine + saponification = 0.25

(c) 1,2-N,N'-bis(2,4,6-triiodo-3-N-acetoxyethylcarbamyl-5-amino benzoyl-diamino-ethane

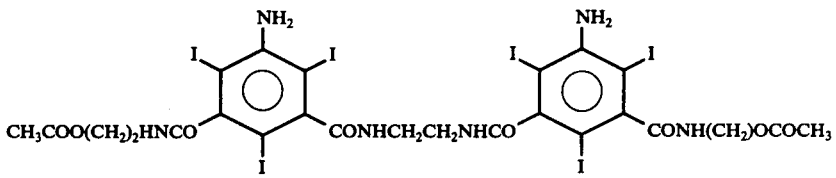

2,4,6-Triiodo-3-N-acetoxyethylcarbamyl-5-amino-benzoic acid chloride (106 g; 0.160 mole) is dissolved in dimethylacetamide (200 ml) and ethylene diamine (10.6 ml; 0.160 mole) is then added dropwise thereto, between 15° and 20° C. After stirring 4 hours at 20°-25° C, ethylene diamine (5.3 ml; 0.080 mole) is added. The solution is then stirred 16 hours at room temperature, after which it is poured over 1 liter ice-water. The resulting precipitate is suction filtered, washed with water and dried, to give 37 g (Yield = 29%) of material the purity of which is controlled by thin-layer chromatography over Silicagel plate in eluent: benzene/methylethylketone/formic acid (60:25:20):
Rf: acid chloride = 0.9
Rf: condensed product: 0.4

(d) 1,2-N,N'-bis(2,4,6-triiodo-3-N-hydroxyethylcarbamyl-5-gluconylamino-benzoyl)-diamino-ethane

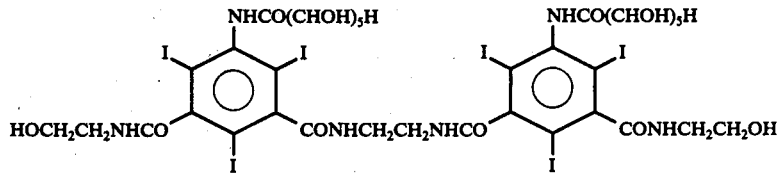

A/ Condensation

The above product (37 g; 0.028 mole) is dissolved in dimethylacetamide (80 ml). Penta-acetyl gluconic acid chloride (47.5 g; 0.112 mole) is added thereto portionwise. After stirring during 3 days at room temperature, the solution is poured over ice-water (500 ml). The resulting gum crystallizes. The precipitate is suction filtered, washed with water and is directly saponified.

B/Saponification

The condensation product is dissolved in 2N sodium hydroxide (150 ml). After stirring 24 hours at room temperature, the solution is made neutral with hydrochloric acid. It is then extracted with 3 × 50 g phenol; the organic phase is washed with 3 × 50 ml water. Diethyl ether (600 ml) is added to the phenol phase which is then extracted with 3 × 150 ml water. The aqueous solution is washed with 3 × 150 ml diethyl ether and is then treated with charcoal 3SA during 24 hours, at room temperature. The resulting material is filtered and evaporated to dryness, to give 15 g (Yield = 30%) 1,2-N,N'-bis(2,4,6-triiodo-3-N-hydroxyethyl-carbamyl-5-gluconylamino-benzoyl)diamino-ethane the purity of which is controlled by thin-layer chromatography over Silicagel plate in the following eluents:

Benzene/methylethylketone/formic acid (60:25:20)
 Rf: starting material = 0.4
 Rf: condensation product = 0.2
 Rf: saponification product = 0.0
Butanol/acetic acid/water (50:11:25)
 Rf = condensation product: 0.85
 Rf = saponification product = 0.15
Isobutanol/isopropanol/ammonia (50:20:30)
 Rf: condensation product = 0.85
 Rf: saponification product = 0.05

EXAMPLE VI

Preparation of 1,2-N-(2,4,6-triiodo-3-N-hydroxyethylcarbamyl-5-gluconylamino-benzoyl)-N'-(2,4,6-triiodo-3-N-methylcarbamyl-5-gluconylamino-benzoyl)-diamino-ethane (a) 3-(2-Amino-ethylcarbamyl)-5-nitro-benzoic acid

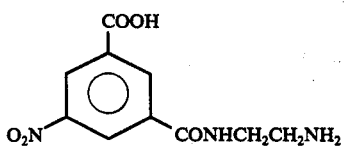

450 g (2 mole) monomethyl ester of nitro isophthalic acid are added portionwise to a solution of ethylene diamine (480 g; 8 moles) in water (400 ml). After stirring 48 hours at room temperature, the precipitate is suction filtered, washed with water and dried, to give 320 g (Yield = 63%) 3-(2-amino-ethylcarbamyl)-5-nitro-benzoic acid. The purity of the product is controlled by:
1. Titration with 0.1N sodium hydroxide = 103%
 with perchloric acid in acetic acid = 103%
2. Thin-layer chromatography in eluent: Benzene/methylethyl ketone/formic acid (60:25:20):
 Rf: starting material = 0.8
 Rf: condensation product = 0.15

(b) 3-(2-Amino-ethylcarbamyl)-5-amino-benzoic acid

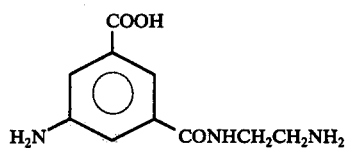

3-(2-Amino-ethylcarbamyl)-5-nitro-benzoic acid (200 g; 0.79 mole) is dissolved in water (1000 ml) and concentrated hydrochloric acid (75 ml). Palladium-over-charcoal (20 g) is added thereto, and the material is hydrogenated in an autoclave during 2 hours, under a hydrogen pressure of 3-4 kg. The resulting material is filtered and evaporated to dryness in vacuo, to give a solid which is taken up into ethanol (500 ml). The resulting precipitate is suction filtered, washed with ethanol and dried, to give 130 g (Yield = 74%) 3-(2-amino-ethylcarbamyl)-5-amino-benzoic acid the purity of which is controlled by:
1. Titration with 0.1N sodium methoxide = 96%
 with perchloric acid in acetic acid = 98%
2. Thin-layer chromatography in eluent: ethyl acetate/isopropanol/ammonia (35:35:40)
 Rf: starting material = 0.55
 Rf: reduced product = 0.3

(c) 2,4,6-Triiodo-3-(2-amino-ethylcarbamyl)-5-amino-benzoic acid

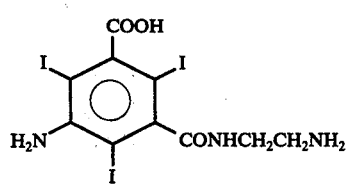

To a solution of 3-(2-amino-ethylcarbamyl)-5-amino-benzoic acid (98 g; 0.38 mole) in water (3 liters) and concentrated hydrochloric acid (38 ml) is added a solution of anhydrous iodine chloride (220 g) in water (500 ml) and potassium chloride (102 g). The resulting mixture is stirred 24 hours at 50° C, and then 24 hours at room temperature. After treatment with bisulfite, suction filtering and washing with water, the resulting material is dissolved in normal sodium hydroxide and the acid is reprecipitated with sulfur dioxide. The precipitate is suction filtered, washed with water and dried, to give 90 g (Yield 40%) of 2,4,6-triiodo-3-(2-amino-ethylcarbamyl)-5-amino-benzoic acid, the purity of which is controlled by:
1. Titration with sodium methoxide (0.1N) = 100%
 Iodine titration = 98%
2. Thin-layer chromatography in eluents:
 Isobutanol/isopropanol/ammonia (50:20:30)
  Rf: starting material = 0.25
  Rf: iodo compound = 0.35
 Butanol/acetic acid/water (50:11:25)
  Rf: starting material = 0.3
  Rf: iodo compound = 0.35

(d)
2,4,6-Triiodo-3-amino-5-[2-(2,4,6-triiodo-3-N-methylcarbamyl-5-amino-benzoyl)amino-ethyl]carbamyl-benzoic acid

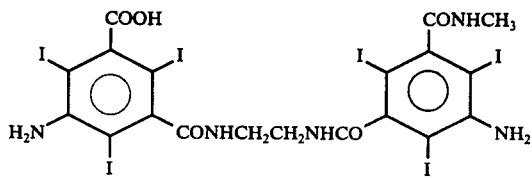

To a suspension of 2,4,6-triiodo-3-(2-amino-ethylcarbamyl)-5-aminobenzoic acid (85 g; 0.142 mole) in dimethylacetamide (200 ml) in the presence of triethylamine (36 g; 0.353 mole) is added 2,4,6-triiodo-3-N-methylcarbamyl-5-amino-benzoic acid chloride (88 g; 0.148 mole). The reaction mixture is heated at 50° C during 16 hours. The solution is poured over water (1000 ml) and, after filtration of a slight amount of insoluble material, is made acidic to pH 1 with concentrated hydrochloric acid. The precipitate is suction filtered, washed with water and dried, to give 140 g of material which is dissolved in normal sodium hydroxide (120 ml); after stirring at room temperature during 5 days, the precipitate is suction filtered and washed with water. The sodium salt is redissolved in water (1200 ml) at 90° C, and is then made acidic to pH 1 with hydrochloric acid. The resulting material is suction filtered, washed with water and dried, to give 68 g (Yield: 39%) 2,4,6-triiodo-3-amino-5-[2-(2,4,6-triiodo-3-N-methylcarbamyl-5-amino-benzoyl)-amino-ethyl]carbamyl-benzoic acid, the purity of which is controlled by:
1. Titration with 0.1N sodium methoxide = 100%
2. Thin-layer chromatography in eluent: benzene/methylethylketone/formic acid (60:25:20):
   Rf: starting amine = 0.05
   Rf: condensation product = 0.45

(e)
2,4,6-Triiodo-3-amino-5-[2(2,4,6-triiodo-3-N-methylcarbamyl-5-amino-benzoyl)-amino-ethyl]carbamyl-benzoic acid chloride

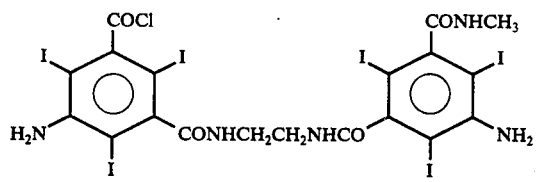

A suspension of 2,4,6-triiodo-3-amino-5-[2-(2,4,6-triiodo-3-N-methylcarbamyl-5-amino-benzoyl)-amino-ethyl]carbamyl-benzoic acid (11.6 g; 0.1 mole) in thionyl chloride (50 ml) is heated during 16 hours. The reaction mixture is then cooled, suction filtered, washed with isopropyl ether (100 ml) and ethyl acetate (100 ml) and dried, to give 10 g (Yield 84%) 2,4,6-triiodo-3-amino-5-[2-(2,4,6-triiodo-3-N-methylcarbamyl-5-amino-benzoyl)-amino-ethyl]carbamyl-benzoic acid chloride, the purity of which is controlled by thin-layer chromatography over Silicagel plate in eluent: benzene/methylethylketone/formic acid (60:25:20):
Rf: starting acid = 0.45
Rf: acid chloride = 0.7
Rf: after condensation with propylamine = 0.65
Rf: after condensation with ethanolamine = 0.30

(f)
1,2-N-2,4,6-triiodo-3-N-hydroxyethylcarbamyl-5-amino-benzoyl)-N'-(2,4,6-triiodo-3-N-methylcarbamyl-5-amino-benzoyl)diamino-ethane

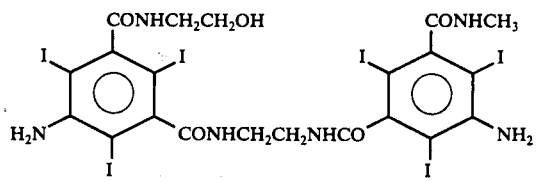

2,4,6-triiodo-3-amino-5-[2-(2,4,6-triiodo-3-N-methylcarbamyl-5-amino-benzoyl)-amino-ethyl]carbamyl-benzoic acid chloride (10 g; 0.0085 mole) is dissolved in dimethylacetamide (20 ml). After cooling to 15° C over a water/ice bath, ethanolamine (1.2 ml; 0.0187 mole) is slowly added thereto. After stirring 48 hours at room temperature, the solution is poured over water (80 ml). The precipitate is suction filtered, washed with water and dried, to give 9.5 g (Yield = 93%) 1,2-N-(2,4,6-triiodo-3-N-hydroxyethyl-carbamyl-5-amino-benzoyl)-N'-(2,4,6-triiodo-3-N-methylcarbamyl-5-amino-benzoyl)-diamino-ethane the purity of which is controlled
1. By thin-layer chromatography over Silicagel plate in eluent: benzene/methylethylketone/formic acid (60:25:20):
   Rf: acid chloride = 0.65
   Rf: condensation product = 0.3
2. By iodine titration: 96%.

(g)
1,2-N-(2,4,6-triiodo-3-N-hydroxyethylcarbamyl-5-gluconylamino-benzoyl)-N'-(2,4,6-triiodo-3-N-methylcarbamyl-5-gluconylamino-benzoyl)-diamino-ethane

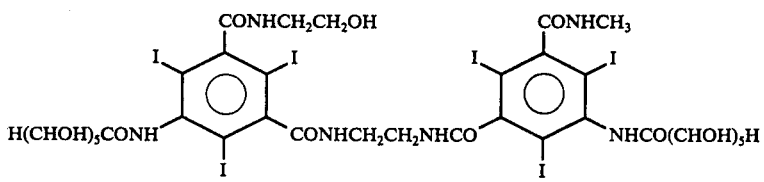

A/ Condensation

The product obtained under (f) (9.5 g; 0.0079 mole) is dissolved in dimethylacetamide (20 ml). Penta-acetyl gluconic acid chloride (13,5 g; 0.0317 mole) is added thereto; after 48 hours at room temperature, a further amount (3.4 g; 0.0079 mole) of penta-acetyl gluconic acid chloride is again added. After stirring 48 hours at room temperature, the solution is poured over 100 ml water. The resulting very hard gum crystallizes. The precipitate is suction filtered, washed with water and dried, to give 12.5 g (Yield = 67%) of material which is directly saponified. Purity control is effected by thin-layer chromatography in eluent: benzene/methylethylketone/formic acid (60:25:20):

Rf: starting material = 0.3
Rf: condensation product = 0.35

B/ Saponification

The condensation product (12.5 g; 0.0053 mole) is dissolved in 2N sodium hydroxide (50 ml). After 24 hours at room temperature, a slight amount of insoluble material is filtered off. The solution is neutralised with hydrochloric acid, extracted with 3 × 20 g phenol, the organic phase is washed with 3 × 20 ml water. Diethylether (250 ml) is added to the phenol phase, which is extracted with 3 × 50 ml water. The aqueous solution is washed with 3 × 100 ml diethyl ether and treated with charcoal 3S A during 24 hours at room temperature. Evaporation to dryness gives 5 g (Yield 54%)

1,2-N-(2,4,6-triiodo-3-N-hydroxyethylcarbamyl-5-gluconylamino-benzoyl)-N-(2,4,6-triiodo-3-N-methylcarbamyl-5-gluconylamino-benzoyl)diamino-ethane the purity of which is controlled by thin-layer chromatography over Silicagel plate in the following eluents:

Benzene/methylethylketone/formic acid (60:25:20): Rf = 0.0
Butanol/acetic acid/water (50:11:25): Rf = 0.1
Isobutanol/isopropanol/ammonia (50:20:30): Rf = 0.05

The compounds of the formula (I) are characterized by particularly low osmolality values and also by a low toxicity.

Results obtained with compounds of the formula (I), as aqueous solutions containing 28% iodine, are set forth in the following Table.

| Compound | Osmolality mosm/kg (28% iodine) | LD$_{50}$, I.V., in mice (g I/kg) | Neurotoxicity | |
|---|---|---|---|---|
| | | | Intra-cisternal injection in rats* | Intra-cerebral injection in mice** |
| Ex. I | 200 | 15 | Death rate: 0% at 50 mg I/rat | Death rate: 0% at 700 mg I/kg |
| Ex. II | 204 | 6 | | |
| Ex. III | 140 | 9 | | |

*Technique according to E. Melartin (Investigative Radiology, 1970, 5, 1, 13-31)
**Technique according to Haley and MacCornick (British Journal Pharacology, 1957, 12, 12-15).

In view of their low toxicity, the compounds of the formula (I) constitute most valuable X-ray contrast media, particularly for myelography and angiography.

The preferred pharmaceutical form of the X-ray contrast materials consists of aqueous solutions of compounds of the formula (I).

The aqueous solutions contain advantageously from 5 g to 100 g of compound of the formula (I) per 100 ml of solution, and the injectable amount of such solutions may vary within the range from 5 ml to 500 ml.

Having now described our invention what we claim as new and desire to secure by Letters Patent is:

1. Compounds having the general formula:

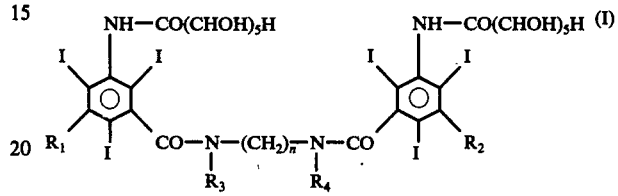

in which:
$n$ is an integer from 0 to 4,
$R_1$ and $R_2$, independently from each other, are selected from the group consisting of a radical of the formula —CONHR$_5$, in which R$_5$ is selected from the group consisting of alkyl having 1-4 carbon atoms and hydroxyalkyl having 1-4 carbon atoms, and a radical of the formula

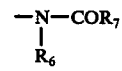

in which R$_6$ and R$_7$ each represent alkyl radicals having 1-4 carbon atoms, and
R$_3$ and R$_4$, independently from each other, are selected from the group consisting of hydrogen and alkyl having 1-4 carbon atoms.

2. 1,2-N,N'-bis(2,4,6-triiodo-3-N-methyl-N-acetylamino-5-N-gluconylamino-benzoyl)diamino-ethane.

3. X-ray contrast medium consisting of an aqueous solution containing 5-100 g of a compound of the formula (I) as claimed in claim 1 per 100 ml of solution.

* * * * *